US009072863B2

(12) United States Patent
Bennett

(10) Patent No.: US 9,072,863 B2
(45) Date of Patent: Jul. 7, 2015

(54) INTRACRANIAL CATHETER AND METHODS OF USE

(75) Inventor: Steven Bennett, Jupiter, FL (US)

(73) Assignee: University of South Florida, Tampa, FL (US)

( * ) Notice: Subject to any disclaimer, the term of this patent is extended or adjusted under 35 U.S.C. 154(b) by 630 days.

(21) Appl. No.: 12/714,927

(22) Filed: Mar. 1, 2010

(65) Prior Publication Data

US 2010/0222764 A1    Sep. 2, 2010

Related U.S. Application Data

(63) Continuation of application No. PCT/US2008/073974, filed on Aug. 22, 2008.

(60) Provisional application No. 60/968,415, filed on Aug. 28, 2007.

(51) Int. Cl.
*A61M 5/142* (2006.01)
*A61M 25/00* (2006.01)
*A61M 25/02* (2006.01)
*A61M 5/145* (2006.01)

(52) U.S. Cl.
CPC ............ *A61M 25/0041* (2013.01); *A61M 5/142* (2013.01); *A61M 25/0021* (2013.01); *A61M 25/02* (2013.01); *A61M 2005/14513* (2013.01); *A61M 2025/0213* (2013.01); *A61M 2210/0693* (2013.01)

(58) Field of Classification Search
CPC ..................... A61M 25/0041; A61M 25/0021; A61M 2210/0693; A61M 2025/0213

USPC .......... 604/500, 506, 264, 523, 533, 534, 535
See application file for complete search history.

(56) References Cited

U.S. PATENT DOCUMENTS

| | | | |
|---|---|---|---|
| 5,445,625 A * | 8/1995 | Voda | 604/532 |
| 5,639,275 A * | 6/1997 | Baetge et al. | 604/891.1 |
| 6,749,574 B2 | 6/2004 | O'Keefe | |
| 7,867,218 B1 * | 1/2011 | Voda | 604/532 |
| 2004/0215162 A1 | 10/2004 | Putz | |
| 2006/0135945 A1 * | 6/2006 | Bankiewicz et al. | 604/506 |
| 2007/0005016 A1 * | 1/2007 | Williams | 604/116 |
| 2007/0088295 A1 | 4/2007 | Bankiewicz | |
| 2007/0167931 A1 * | 7/2007 | Waller et al. | 604/533 |
| 2008/0300571 A1 * | 12/2008 | LePivert | 604/503 |

OTHER PUBLICATIONS

Bundgaard, Means to Enhance Penetration, Prodrugs as a means to Improve the Delivery of Peptide Drugs, Advanced Drug Delivery Reviews, 1992, vol. 8, pp. 1-38.

(Continued)

*Primary Examiner* — Theodore Stigell
*Assistant Examiner* — Benjamin Koo
(74) *Attorney, Agent, or Firm* — Nilay J. Choksi; Ronald E. Smith; Smith & Hopen, P.A.

(57) ABSTRACT

A catheter assembly for intracranial treatment of a subject that includes an outer tube that may be connected to an infusion or osmotic pump and delivered through a bendable catheter to the target brain site of the subject. The assembly facilitates regular accurate placement of drug or compound delivery at the tissue region without additional contact and minimizes trauma to the subject.

5 Claims, 3 Drawing Sheets

(56) References Cited

OTHER PUBLICATIONS

Kakeya et al., Studies on Prodrugs of Cephalosporins. I. Synthesis and Biological Properties of Glycyloxybenzoyloxymethyl and Glycylaminobenzoyloxymethyl Esters of 7 Beta-[2-(2-Aminothiazol-4-yl)-(Z)-2-methoxyiminoacetamido]-3-methyl-3-cephem-4-carboxylic Acid, Chem. Pharm. Bull., 1984, vol. 32, No. 2, pp. 692-698.

Bungaard, A Textbook of Drug Design and Development, Chapter 5, 1991, Harwood Academic Press, Philadelphia, pp. 113-191.

Nielsen et al., Glycolamide Esters as Biolabile Prodrugs of Caroxylic Acid Agents: Synthesis, Stability, Bioconversion, and Physicochemical Properties, Journal of Pharmaceutical Sciences, 1988, vol. 77, No. 4, pp. 285-298.

* cited by examiner

INTRACRANIAL CATHETER AND METHODS OF USE

CROSS-REFERENCE TO RELATED APPLICATIONS

This application is a Continuation of currently pending PCT Application PCT/US2008/073974 filed Aug. 22, 2008, which claims priority to U.S. Provisional Patent Application No. 60/968,415, filed Aug. 28, 2007; which applications are fully incorporated herein.

BACKGROUND OF THE INVENTION

1. Field of the Invention

This invention relates to a method of treating a neurological disease or other disease of the brain or central nervous system and more specifically relates to delivering therapeutic agents directly into the central nervous system or specific brain structures.

2. Brief Description of the Prior Art

A problem with orally administered drugs is unpleasant side effects including severe nausea and gastric ulcers which patients develop following chronic use. Further, with chronic oral therapy the therapeutic value diminishes over time requiring dose escalation. In addition, limited transport of drugs across the blood brain barrier increases the potential for systemic adverse side-effects. Moreover, delivery of a drug directly to the brain has an advantage of a direct target and minimizes other side effects and systemic problems throughout the body or other areas of the body which are not affected by neurological pathology.

Therefore, there is a continuing significant need in the field of intracranial treatment, particularly with insertion of catheters into the interior of the brain, for improvements in accuracy of insertion and avoidance of injury, while retaining efficiency and ease of use for effective treatment of neurological disorders including Alzheimer's without the side effects and problems encountered with standard drug delivery.

There is also a need in the field of intracranial treatment to minimize invasiveness and to reduce the number of instruments which penetrate brain tissue or the number of times a single instrument must penetrate brain tissue.

Furthermore, there is a need in the field of intracranial treatment to provide the ability to precisely locate the position of a catheter during insertion to ensure proper positioning.

The present invention relates to the intracranial transfer of drugs or fluids or liquid based materials and, in particular, to devices for effecting such transfer.

SUMMARY OF THE INVENTION

The long-standing but heretofore unfulfilled need for an improved intracranial catheter assembly is now met by a novel assembly. The novel assembly enables precise treatment and delivery of a preselected compound or material having a liquid base to an area or areas of brain tissue in a subject comprising a mammal such as a rodent (mouse, guinea pig, or rat). The catheter assembly of this invention overcomes certain problems and shortcomings of the prior art and provides a unique structure satisfying a number of specific intracranial treatment needs. The preferred embodiment of the invention enables the catheter assembly to be placed subcutaneously in a subject for treatment and therapy but allows the subject to live following removal of the catheter assembly.

The novel catheter assembly comprises catheters of different lengths and having different arrangements of ports to provide for treatment of specific desired tissue regions in the brain. In one alternate embodiment, the catheter is connected to a conventional osmotic or infusion pump with a polyethylene tube having an internal diameter of 0.011 inches and an outer diameter of 0.024 inches. A tube in the form of a stainless steel 29 or 30 gauge tube has a proximal end disposed within and secured to the lumen of the polyethylene tube. The distal end of the second tube is positioned external to the lumen of the polyethylene tube and is bent a first time at an angle of about one hundred fifty degrees (150°) and a second time at approximately ninety degrees (90°) to allow access to the hippocampus region of the brain of the subject.

In a preferred embodiment, the subject's skull is drilled and a small hole is created in the brain tissue where the cannula (catheter) is placed and affixed with an adhesive and capped with a round piece of Nitrile. The Nitrile keeps the scalp from adhering to the skull. The novel catheter includes an outer tube having a diameter along its length, an inner tube ensleeved within a lumen of the outer tube, said inner tube having a diameter along its length that is less than an internal diameter of the outer tube, and a bendable, small gauge tube ensleeved within a lumen of the inner tube. The bendable, small gauge tube has a diameter along its length that is less than an internal diameter of the inner tube. The small gauge tube delivers a compound to the brain of a subject. The catheter has a first end connected to a pump to facilitate regular and accurate placement of a drug or compound delivery at a preselected brain tissue region so that, after a second end of the catheter is connected to the preselected brain site, there is no further need for further contact with brain tissue to thereby minimize trauma to the subject. The method includes the steps of ensleeving the inner tube within a lumen of the outer tube, ensleeving the bendable, small gauge tube within a lumen of the inner tube, and delivering a compound to the brain of the subject using the bendable, small gauge tube.

It is an object of the invention to provide an improved intracranial insertion device that reduces injury to the animal Another object of the invention is to provide a catheter assembly that is simple in structure and operation in order to facilitate intracranial procedures.

Another object of the invention is to provide a catheter assembly that enables precise insertion of drug delivery ports or contacts in the brain while avoiding extensive trauma to and scarring of brain tissue or skull.

Another object and a major advantage to the novel system is to enable the use of more than one pump so that more than one compound can be infused simultaneously into different hemispheres of the brain or different regions of the brain in the same hemisphere.

For example, an untreated control in the experiment can be the other brain hemisphere receiving only vehicle whereas it would usually be an aged matched control littermate, ultimately requiring fewer animals for an experiment. The catheter can be bifurcated for multiple dosing regimen. Moreover, the catheters are strongly affixed so that pumps may be changed while the catheters stay in place if studies are run for long periods of time up to several months. However, the apparatus can also be completely removed without permanent damage to the animal which is a clear advantage over prior art catheters. The use of the nitrile cap prevents adhesive coming into contact with the scalp, which would otherwise kill the tissue and cause severe scarring. Prior art devices often leave a crater when the catheter is removed and often cause permanent motor dysfunction. Moreover, prior art catheters frequently become entangled in the cage or provide the animal with access to the tubing, which is commonly chewed through. Therefore, the present invention has clear advantages over the prior art.

These and other objects of the invention will be apparent from the following descriptions and from the drawings.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment. In the drawings.

DETAILED DESCRIPTION OF THE PREFERRED EMBODIMENT

Figure 1:
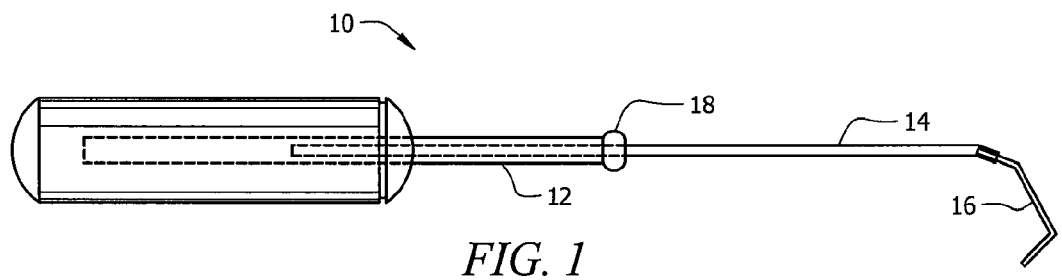
FIG. 1 is a side elevational view of the novel catheter assembly.

Referring now to FIG. 1, it will there be seen that an illustrative embodiment of the novel catheter assembly is denoted as a whole by the reference numeral 10.

Novel catheter assembly 10 enables intracranial treatment of an animal by providing a first, outer large diameter tube 12 made of vinyl tubing, a second, smaller diameter polyethelene tubing 14 and a third, still smaller in diameter steel 29 or 30 gauge tube 16.

Third tube 16 has a proximal end received within and secured to the lumen of second tube 14. The distal end of third tube 16 is external to said second tube and is bent a first time at an angle of about one hundred fifty degrees (150°) and bent a second time to a desired angle, generally ninety degrees (90°), to reach the brain tissue of choice.

Figure 2A:
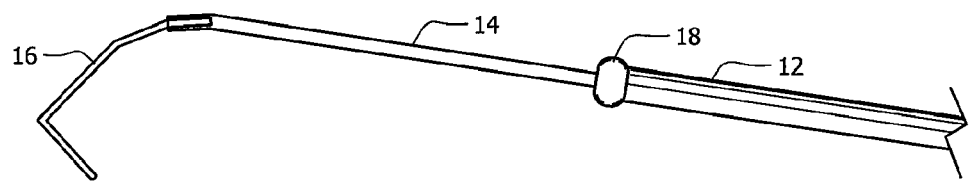
FIG. 2A is a side elevational view, broken-away, of said catheter assembly.

As depicted in FIG. 2A, third tube 16 extends from the lumen of second tube 14 and said second tube extends from the lumen of first tube 12. As can be seen in FIGS. 1 and 2A-2C, second tube 14 includes an obtuse bend at its distal end, resulting in third tube 16 extending distally from the lumen of second tube 14 at an angle. Adhesive 18 is applied to the distal end of first tube 12 and to second tube 14 to prevent telescopic displacement of said first and second tubes relative to one another.

Figure 2B:
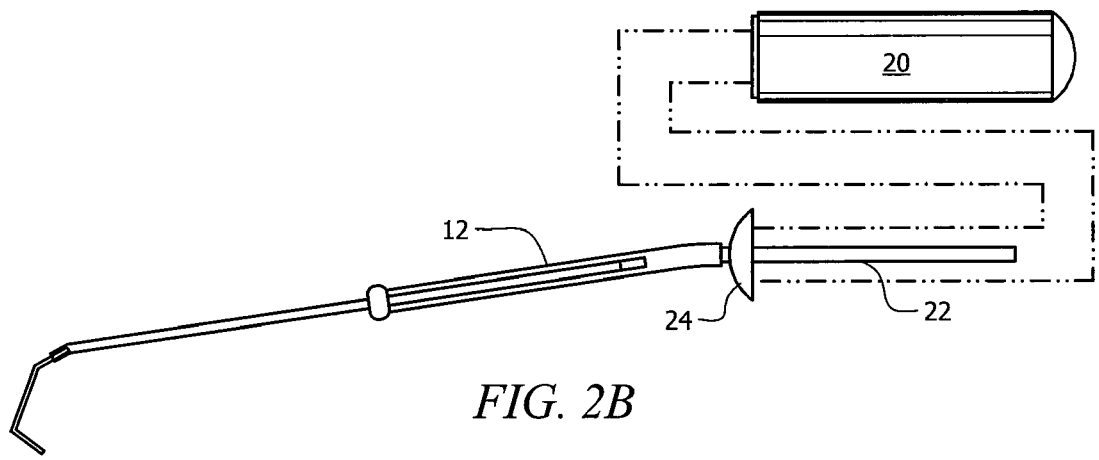
FIG. 2B is a side elevational, exploded assembly view of said catheter assembly.
Figure 2C:
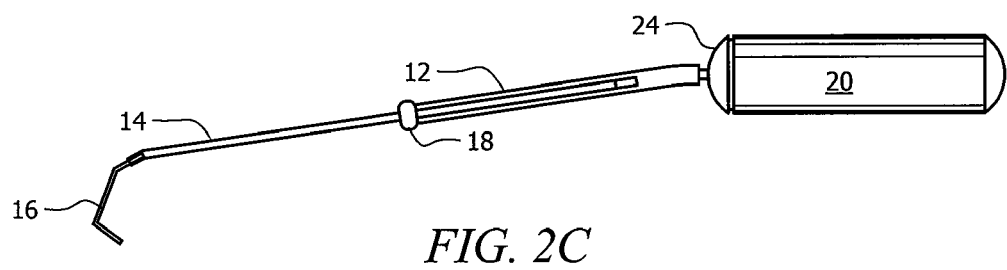
FIG. 2C is a side elevational view of the catheter when assembled.

FIG. 2B depicts the pump end of the novel catheter when the catheter is attached to a generic small infusion or osmotic pump at the vinyl tube end. More particularly, it depicts the proximal or pump end of first tube 12 positioned adjacent a generic small infusion or osmotic pump 20. First tube 12 is secured to pump tube 22 that is positioned within the hollow interior of pump 20 when said pump is assembled as depicted in FIG. 2C. Cap 24 limits the depth of insertion of pump tube 22.

FIG. 2C depicts the completely assembled catheter. The pump holds the liquid based drug or material such as compounds, biologicals or dyes.

Two catheters were placed in different target regions of a female mouse brain. The novel catheters are placed in the region of interest in the brain. The implanted catheter remains implanted intact in the animal after the surgical site is closed for the period of infusing and testing.

Figure 3A:
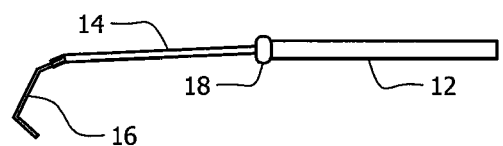
FIG. 3A is a side elevational view of an alternate embodiment of the invention.

FIG. 3A depicts an alternate embodiment of the invention including a silicone 047 sleeve that enshrouds and fits the flow modulator end of the osmotic pump. The same silicone 047 sleeve also enshrouds a polyethylene size 50 tube (PE-50). The length of the silicone 047 sleeve is approximately 2.5 cm. The PE-50 tube is shorter than the silicone sleeve at the area where the flow modulator is connected to provide a snug fit of the silicone tube over the modulator as well. The other end of the PE-50 tube is welded to a polyethylene size 10 tube (PE-10) that enshrouds the 30 gauge catheter. The catheter has a custom bend for delivery of material to the desired site. The 30 gauge catheter comes in contact with the brain tissue for delivery of the drug or desired compound.

Figure 3B:
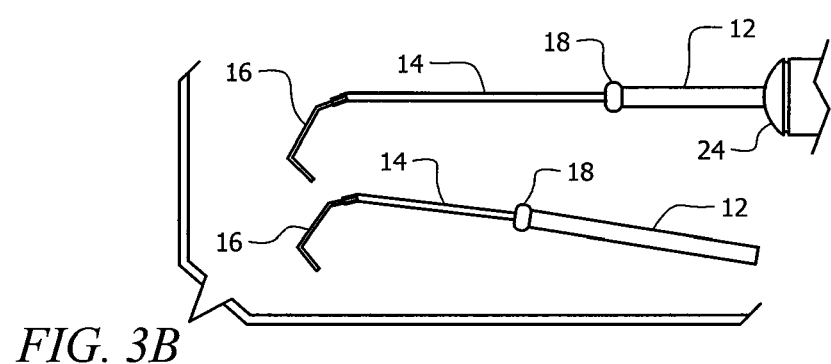
FIG. 3B is a side elevational view depicting the catheter attached to a standard osmotic pump.

FIG. 3B depicts the catheter attached to a standard osmotic pump.

Novel catheter assembly 10 is capable of delivering therapeutic amounts of drugs or biologicals including but not limited to polypeptides, polynucleotides, peptidometics, mimetics, and other desired molecules or compounds as necessitated by the subject for therapy of any neurological disorders.

Infusion of FD & C Blue #1 dye or methylene blue dye is an example of the successful implementation of this catheter in a female mouse. The animal's right hippocampus was infused in two areas. This ability to infuse more than one area at a time is a major feature of this invention. Many different cannulae can be used simultaneously with the novel catheter system using different compounds or by using bifurcated cannulae attached to a single pump. The coordinates of the anterior portion were (from Bregma) Anterior-Posterior=−0.9 mm, Medial-Lateral (ML)=+/−0.6 mm, and depth of 2.0 mm while the posterior cannula was placed AP −2.5 mm, ML+/−0.6 mm, depth 2.5 mm. These coordinates vary given the size or gender of the animal and specific region or regions of interest. The coordinates described herein were for a 25 gram female mouse.

The delivery of a compound, ACT antibody, to the site of interest in the brain is successfully achieved using an alternate embodiment of the invention.

As aforesaid, the novel system enables the use of more than one pump so that more than one compound can be infused simultaneously into different hemispheres of the brain or different regions of the brain in the same hemisphere.

For example, an untreated control in the experiment can be the other brain hemisphere receiving only vehicle whereas it would usually be an aged matched control littermate, ultimately requiring fewer animals for an experiment. The catheter can be bifurcated for multiple dose regimen. Moreover, the catheters are strongly affixed so that pumps may be changed while the catheters stay in place if studies are run for long periods of time up to several months. However, the apparatus can also be completely removed without permanent damage to the animal which is a clear advantage over prior art catheters. The use of the nitrile cap prevents adhesive coming into contact with the scalp, which would otherwise kill the tissue and cause severe scarring. Prior art methods often leave a crater when the catheter is removed and often cause permanent motor dysfunction.

Moreover, prior art catheters frequently become entangled in the cage or provide the animal with access to the tubing. This enables the animal to chew through the tubing. Therefore, the present invention has clear advantages over the prior art.

As used in this disclosure, the term "neural cell" means any cell of neurological origin (brain, spinal cord) including sensory, transmittal and motor cells from the central nervous system or the peripheral nervous system such as a neuron, a glial, astrocyte, etc.

While the invention has been described with respect to specific embodiments by way of illustration, many modifications and changes will occur to those skilled in the art. It is, therefore, to be understood that the appended claims are intended to cover all such modifications and changes as fall within the true scope and spirit of the invention.

What is claimed is:

1. A method of treating a subject having a neurological disorder by targeting a hippocampus in a brain, comprising the steps of:
providing an outer tube;
providing an inner tube;
ensleeving said inner tube within a lumen of said outer tube, said inner tube extending distally from said lumen of said outer tube,
said inner tube having an diameter along its length that is less than an internal diameter of said outer tube, such that said inner tube can be ensleeved within and extend distally from said lumen of said outer tube,
said inner tube having a proximal end and a distal end, said distal end of said inner tube having an obtuse bend;
providing a bendable, small gauge tube;
ensleeving said bendable, small gauge tube within a lumen of said inner tube, said small gauge tube extending distally from said lumen of said inner tube at an angle resulting from said obtuse bend at said distal end of said inner tube, such that a distal end of said small gauge tube is external to said inner tube;
said bendable, small gauge tube having an diameter along its length that is less than an internal diameter of said inner tube, such that said bendable, small gauge tube can be ensleeved within and extend distally from said lumen of said inner tube,
manipulating said bendable, small gauge tube into a plurality of bends that are structured to permit said catheter to reach and deliver a substance to said hippocampus in said brain, said plurality of bends consisting of a first bend at an angle of about 150° and a second bend at an angle of about 90°, said second bend being distal to said first bend along an extent of said small gauge tube;
coupling a pump tube to a proximal end of said outer tube;
positioning a cap near the connection between said pump tube and said outer tube; and
coupling an infusion or osmotic pump to said cap, such that said pump tube is positioned within a hollow interior of said infusion or osmotic pump, said hollow interior of said infusion or osmotic pump holding said substance to be delivered to said hippocampus in said brain,
said substance being liquid based and selected from the group consisting of a compound, a biological, and a dye for treating said neurological disorder; and
using more than one of said catheter on said brain of said subject, whereby a first of said substance may be delivered to a first region of the brain of the subject and a second of said substance may be delivered to a second region of the brain of the subject wherein said first substance does not mix with said second substance.

2. The method of claim 1, wherein:
said first region of the brain of the subject is located in a first hemisphere of the brain of the subject; and
said second region of the brain of the subject is located in a second hemisphere of the brain of the subject.

3. The method of claim 1, wherein:
said first region of the brain of the subject is located in the first hemisphere of the brain of the subject; and
said second region of the brain of the subject is located in the first hemisphere of the brain of the subject.

4. The method of claim 1, wherein:
said first region of the brain of the subject is located in a first hemisphere of the brain of the subject; and
said second region of the brain of the subject is located in a second hemisphere of the brain of the subject.

5. The method of claim 1, wherein:
said first region of the brain of the subject is located in the first hemisphere of the brain of the subject; and
said second region of the brain of the subject is located in the first hemisphere of the brain of the subject.

* * * * *